United States Patent
Nastasi

(10) Patent No.: US 6,238,652 B1
(45) Date of Patent: May 29, 2001

(54) SYSTEM AND METHOD FOR COLORING AND CONDITIONING NAILS

(76) Inventor: Lisa Rose Nastasi, 118 W. 79th St., New York, NY (US) 10024

(*) Notice: Subject to any disclaimer, the term of this patent is extended or adjusted under 35 U.S.C. 154(b) by 0 days.

(21) Appl. No.: 09/473,226

(22) Filed: Dec. 27, 1999

(51) Int. Cl.[7] ....................................... A61K 7/04
(52) U.S. Cl. .............................. 424/61; 424/401
(58) Field of Search ....................... 424/61, 401

(56) References Cited
U.S. PATENT DOCUMENTS 5,945,409 * 8/1999 Crandall ................................. 514/78

* cited by examiner

Primary Examiner—Thurman K. Page
Assistant Examiner—S. Howard
(74) Attorney, Agent, or Firm—Mauro Premutico

(57) ABSTRACT

The present invention relates to an improved method for coloring and conditioning nails and an improved combination of agents for coating nails. In one preferred embodiment, a multi-compartment case is provided having multiple conditioning creams and multiple top coats whereby the conditioning creams and top coats are combined to provide different aesthetic appearances. In the preferred embodiment the conditioning cream is rubbed onto a nail surface and comprises aloe vera, collagen, jojoba oil, lanolin, vitamin E, mica and wheat germ oil.

10 Claims, No Drawings

SYSTEM AND METHOD FOR COLORING AND CONDITIONING NAILS

FIELD OF USE

This invention relates generally to an improved method for coloring and conditioning nails and more specifically to a new combination and method for coloring and moisturizing nails which is characterized by ease of use and extended life.

BACKGROUND OF THE INVENTION

It is known that fingernails and toenails should be well maintained for reasons of health and aesthetic appearance. The common regiment used to attain desired aesthetic appearance, color and conditioning of nails, however, is not simple. The steps are numerous and cumbersome. The nails, cuticles and surrounding areas must be trimmed, smoothed and conditioned prior to treatment. This requires the use of numerous accessories in addition to tedious and time consuming application of products and treatments, i.e., soaking of nails in conditioning liquids, application of multiple base coats, colors and top coats. It is for this reason that nail salons are very popular in most urban areas. Unfortunately, processes used by these salons are also time consuming and expensive, and do not provide a simple and easy system with which customers can change the aesthetic appearance of their nails.

To the extent a user desires to condition nails on her own, many conditioners require that the conditioner be permitted to stay overnight on the naked nail without the application of a nail polish. This is obviously a time consuming and inconvenient method requiring multiple steps extended over long periods of time.

It is an object of the present invention to provide a simplified method and system for coloring and conditioning nails.

It is a further object of this invention to provide a method for coloring a nail by using an improved conditioning base followed by a fast drying color and top-coat wherein the color of the nail can be enhanced by both the conditioning coat and the top coat. It is a further object of this invention to provide an improved nail conditioning coat which conditions the nail with an easy to apply base coat.

SUMMARY OF THE INVENTION

An improved method and system for coloring and conditioning nails is described. In a preferred embodiment, a coloring and conditioning crème is first applied onto a nail surface. The crème includes a water based moisturizer, a conditioning oil and mica to provide color and to function as a binding agent for the water based moisturizer and oil based conditioning agent. Preferably, the crème is provided in multiple colors and serves as a coloring agent to the nail process. A top-coat is then applied which is preferably a sheer color to permit the color of the conditioning crème to be visible through the top coat layer. The creme can be uniquely blended by the user to create individual colors.

DETAILED DESCRIPTION OF THE PREFERRED EMBODIMENTS

The present invention uses a rub-on conditioning crème that may be easily rubbed onto the nail without a special applicator. The crème serves as conditioning agent for moisturizing the nail to keep it from drying out. The conditioning crème can also be formulated in accordance with the present invention to carry nutrients which are absorbed by the nail. These nutrients make the nail healthier and stronger. The crème can also be formulated to provide a coloring effect which may work together with a traditional top coat layer having a sheer color arrangement to provide a color combination on the nail. This mixture may be modified to provide numerous different color schemes.

In a preferred embodiment, the rub-on crème includes the following components: Vitamin e, aloe vera, collagen, jojoba oil, lanolin, wheat germ oil, and mica. The ingredients are combined and placed in a container designed to receive the tip of a finger for receiving the mixture without causing unnecessary waste or discomfort to the user. It is preferred that the container include multiple color cremes which permit the user to select or otherwise combine colors to generate a unique color scheme for the individual user. In the preferred embodiment the cremes are provided in multiple square arrangements, however, the cremes can be placed in any preferred scheme which is convenient to the user and for manufacturing. It is preferred that the container top have a least one portion which is transparent to permit the user to view the color and nature of the content prior to opening.

The components may be mixed in any number of ways, as is well known in the art. In the preferred embodiment, the mixture uses about 22% mica by weight to function as a binder between the conditioning oils and water based moisturizing crèmes. In addition, the crème may be modified to include any number of common anti-fungal agents. This would permit the crème to function as a carrier of the anti-fungal agent while providing its conditioning and moisturizing function.

The creme may be applied in any number of ways. However, the crème is designed to be applied using no accessories if so desired by the user. This permits reduction of applicators needed by a user and ease of application. In the preferred method, the crème is applied with the tip of a finger onto a clean nail surface using short light repetitive strokes onto the finger nail in the longitudinal direction of the nail surface. Because of the nature of the crème, application of the crème onto non-nail surfaces is not an issue. The crème will not bind to the skin and can be simply removed off the skin with a tissue, cotton swab or rubbed off with a finger. No special removers or cleaners need to be used. Water may be used to clean overexposed areas.

Once the crème is applied to the nails, a top coat is applied in its common manner. The top coat serves to bind the crème onto the nail surface and enhance and vary color. The latter function is preferably served by using a sheer top coat which permits the color scheme of the crème to show through the top coat. Accordingly, any manner of coloring agents may be added to the crème to provide improved aesthetic effect to the combined crème and top coat.

Alternatively, the crème could be applied using any number of applicators. It would be preferred that the applicator permit ample removal of the crème from its container and application onto the nail surface. The applicator would most likely be preferred in salons and other cases wherein the same container will be used for multiple users. Accordingly, it would be preferable that the applicator be a single use, disposable applicator.

The preferred formulation for the crème discussed above may be modified in any number of ways. In another preferred embodiment, the crème includes one or more conditioning oils and one or more moisturizing agents, in addition to the mica. The conditioning oils are preferably selected from the form group comprising vitamin E, wheat germ oil, lanolin and jojoba oil. The moisturizing agent may be selected from the group comprising aloe vera and collagen. These agents and oils are exemplary, and alternatives would be known to those skilled in the art once viewed in light of the teachings of the present invention.

In addition to the above modifications, the crème may also be modified to include at least one anti-fungal crème. This would serve as either a preventative or medicinal function. Undesired fungal growth on nail surfaces are not uncommon. A need exists therefore, for anti-fungal action by a condition/moisturizing crème. As noted above, coloring agents could also be added to provide coloring effects and accents. As used herein color also includes a clear value.

In an alternative embodiment, a clear base crème is provided in conjunction with a color top coat for coloring of the nail. Alternatively, the base creme could be used to itself provide multiple coloring agents. A container would be provided having a crème agent and multiple compartments holding multiple coloring agents. A user would apply the crème onto the nail then mix a coloring agent onto the nail surface and then apply a sheer top coat to permit the coloring agent to modify the appearance of the nail.

In an alternative embodiment of the present invention, non-lacquer water based nail crème were prepared in accordance with the following formulations:

| Ingredients | Formula A | Formula B | Formula C | Formula D | Formula E |
|---|---|---|---|---|---|
| Phase A | | | | | |
| Deionized Water | 58.95 | 53.45 | 48.45 | 48.70 | 49.40 |
| Propylene Glycol | 3.00 | 3.00 | 0.00 | 0.00 | 0.00 |
| Glycerine | 2.00 | 2.00 | 5.00 | 0.00 | 0.00 |
| Glycereth-26 (Protochem Gl-26) | 0.00 | 0.00 | 0.00 | 5.00 | 5.00 |
| Veegum Ultra (Vanderbilt) | 0.40 | 0.40 | 0.40 | 0.40 | 0.00 |
| Aloe Extract | 0.50 | 0.50 | 0.50 | 0.50 | 0.50 |
| Hydroxypropylmethyl-cellulose (J76MS Dow) | 0.10 | 0.10 | 0.10 | 0.10 | 0.10 |
| Triethanolamine 99% | 1.00 | 1.00 | 1.00 | 0.50 | 0.50 |
| Phase B | | | | | |
| Polythylene Homopolymer 6A (Allied signal) | 2.00 | 2.00 | 2.00 | 2.00 | 2.00 |
| Ganex V220 (ISP) | 1.00 | 1.50 | 1.50 | 1.25 | 1.25 |
| 2 Pryrollidone, 1 Ethenyl-Polymer, 1-Eiconsene | 3.00 | 3.00 | 3.00 | 3.00 | 3.00 |
| Stearic Acid | | | | | |
| Sorbitan Stearate (Span 60) | 2.00 | 2.00 | 2.00 | 2.00 | 2.00 |
| Glyceryl Stearate (GMS Pure 450 Protameen) | 4.00 | 4.00 | 4.00 | 4.00 | 4.00 |
| Lanolin | 2.00 | 2.00 | 2.00 | 2.00 | 2.00 |
| Isodecyl Neopentanoate (Bernel 105) | 2.50 | 2.50 | 2.50 | 3.00 | 3.00 |
| Avocado Oil | 0.10 | 0.10 | 0.10 | 0.10 | 0.10 |
| Wheat Germ Oil | 1.00 | 1.00 | 1.00 | 1.00 | 1.00 |
| Grape Seed Oil | 0.10 | 0.10 | 0.10 | 0.10 | 0.10 |
| Jojoba Oil | 0.20 | 0.20 | 0.20 | 0.20 | 0.20 |
| Tocopheryl Acetate | 0.10 | 0.10 | 0.10 | 0.10 | 0.10 |
| Retinyl Palmitate | 0.05 | 0.05 | 0.05 | 0.05 | 0.05 |
| Phase C | | | | | |
| Pigment | 25.00 | 25.00 | 25.00 | 25.00 | 25.00 |
| Phase D | | | | | |
| Germaben II (Preservative) (ISP) | 1.00 | 1.00 | 1.00 | 1.00 | 1.00 |

The above formulations are all set forth in percentage terms by (weight) (volume). The pigments can be of any suitable type. Pigments which were found to be acceptable were timica based pigments available from the Engelhard Corporation, Iselin, N.J. 08830. These colorants were found to be pearlescent and iridescent and did not stain the nails upon the application of the crème. The following colorants were found to be useful: Cloisonne Satin Colors, Flamenco Satin Colors, Flamenco Pearl and Colors, Gemtone Colors, Cloisonne Colors Timica Lustre Pigments and Douchrome Irridescent Colors.

The above formulations were found to provide a cream coloring system that could be applied directly to the nails and then be finished off with a top coat of nail lacquer for protection.

The manufacturing procedure consisted of the following procedure:

Adding Deionized Water in a mixing vessel. Adding the ethydroxymethylcellulose and warming slightly while mixing until a clear solution is obtained. Veegum Ultra is then added as the mixing is continued and the temperature is raised to 80 deg. C. Mixing should continue until the Veegum is dispersed. The Glycereth-26, Aloe Extract, pigment and Triethanolamine are then individually added mixed into the same vessel and while maintaining the temperature at 80° C.

The emulsion is formed by combining the contents of the first vessel with the contents of a second vessel which includes all the elements of Phase B. The Phase B elements are combined in a separate vessel which is heated up to 80 C. as the ingredients are mixed. As the mixture of the combined vessels cool off to about 60 C., the Germaben II is mixed into the mixture until a uniform mixture is attained. The mixture is then permitted to cool down to room temperature which creates a thick crème suitable for placement into jars.

The inventor has also developed a non-lacquer anhydrous nail coloring crème. The following formulations were used:

| Ingredients | Formula A | Formula B | Formula C | Formula D |
|---|---|---|---|---|
| Octyl Stearate | 48.80 | 46.10 | 38.10 | 00.00 |
| Oleyl Alcohol | 00.00 | 00.00 | 00.00 | 46.10 |
| Tocopheryl Acetate | 0.40 | 0.40 | 0.40 | 0.40 |
| Jojoba Oil | 4.00 | 4.00 | 4.00 | 4.00 |
| Isostearyl Neopentanoate | | | | |
| Ozokerite | 2.00 | 2.00 | 2.00 | 2.00 |
| Polythylene Homopolymer 6A (Allied Signal) | 11.00 | 11.00 | 11.00 | 11.00 |
| Lanolin | 2.15 | 2.40 | 2.40 | 2.40 |
| Ganex V220 (ISP) | 0.75 | 1.00 | 1.00 | 1.00 |
| 2 Pryrollidone, 1 EthenylPolymer, 1-Eicosene | 0.10 | 0.10 | 0.10 | 0.10 |
| Propyl Paraben | | | | |
| Pigment | 30.00 | 32.00 | 40.00 | 32.00 |

The above ingredients are combined as follows: All the ingredients except for the pigment are mixed in a vessel heated to 85 C. until they are completely melted. The pigment is then mixed in until it is completely dispersed and smooth. The temperature is then maintained for about 15 to thirty minutes and then poured into a container while heated.

The above has been a description of the preferred embodiments of the present invention and should not be construed as limiting the scope of the claims which define the invention. Many modifications to the invention would be obvious to those skilled in the art in view of the teaching of the present invention. The claims should be construed where applicable to cover such modifications.

What is claimed is:

1. A method for treating a nail, said method comprising the steps of:
   a) rubbing a color and conditioning cream onto the nail, said cream comprising mica, vitamin E and aloe vera; and
   b) applying a top coat on said conditioning cream.

2. The method of claim 1 wherein the cream further includes at least one of the following aloe vera, collagen, jojoba oil, lanolin and wheat germ oil.

3. The method of claim 1 wherein the conditioning cream further includes aloe vera, collagen, jojoba oil, lanolin and wheat germ oil.

4. The method of claim 1 wherein the top coat is a tinted color such that the conditioning cream is visible after the application of the top coat and the combination thereof produces an enhanced aesthetic appearance of the nail finish.

5. The method of claim 1 wherein the conditioning cream includes at least 20% of mica by weight.

6. A container for supplying nail treatment products, said container comprising a plurality of compartments comprising at least one conditioning cream for direct application onto a nail surface and at least one top coat for application onto said conditioning cream.

7. A nail conditioning creme for direct application onto a nail, said crème comprising;
   a) a water based moisturizer having at least one water based moisturizing agent selected from the group consisting of aloe vera and collagen;
   b) a conditioner having at least one conditioning agent selected from the group consisting of jojoba oil, lanolin, vitamin E and wheat germ oil; and
   c) mica.

8. The conditioning crème of claim 7 further comprising an anti-fungal agent.

9. A method for conditioning and coloring nails, said method comprising the steps of:
   a) Applying a water based coloring conditioner onto a nail, said conditioner including a water based moisturizing agent, a conditioning agent and mica; and
   b) applying a top coat onto the water based conditioner.

10. The method of claim 9, wherein the water based conditioning crème includes at least one oil based moisturizing agent.

* * * * *